United States Patent [19]

Yokota et al.

[11] Patent Number: 5,059,592

[45] Date of Patent: Oct. 22, 1991

[54] COMPOSITION FOR PREVENTION AND (OR) TREATMENT OF AIDS

[75] Inventors: Yoshiko Yokota, Ibaraki; Yasuhiro Mine, Osaka; Yoshimi Wakai, Toyonaka, all of Japan

[73] Assignee: Fujisawa Pharmaceutical Co., Ltd., Osaka, Japan

[21] Appl. No.: 221,518

[22] Filed: Jul. 20, 1988

[30] Foreign Application Priority Data

Jul. 29, 1987 [GB] United Kingdom ............. 8717955

[51] Int. Cl.$^5$ ............................................. A61K 31/70
[52] U.S. Cl. ........................................ 514/50; 514/18
[58] Field of Search .................................. 514/18, 50

[56] References Cited

U.S. PATENT DOCUMENTS 4,322,341  3/1982  Kitaura et al. .
4,666,889  5/1987  Mine et al. .

OTHER PUBLICATIONS

Marketletter, May 4, 1987.

Primary Examiner—Robert A. Wax
Assistant Examiner—Fred Tsung
Attorney, Agent, or Firm—Oblon, Spivak, McClelland, Maier & Neustadt

[57] ABSTRACT

A method for treatment of Lymphadenopathy which comprises administering FK-565 or its pharmaceutically acceptable salt and AZT in a ratio of about 1:10–2,000 by weight to an individual in need therefore.

7 Claims, No Drawings

COMPOSITION FOR PREVENTION AND (OR) TREATMENT OF AIDS

This invention relates to a new composition for prevention and (or) treatment of aquired immunodeficiency syndorome (AIDS), AIDS related complex (ARC) and Lymphadenophathy (LA). More particularly, it relates to a new composition for prevention and (or) treatment of AIDS, ARC and LA which comprises, as effective ingredients, FK-565 or its pharmaceutically acceptable salt and 3'-azido-3'-deoxythymidine, and to methods for prevention and treatment of AIDS, ARC and LA, which comprise administering FK-565 or its pharmaceutically acceptable salt and 3'-azido-3'-deoxythymidine to human beings.

3'-Azido-3'-deoxythymidine (hereinafter referred to merely AZT) is known as an effective drug in treatment of AIDS.

A few years ago, it was found that AZT could act as a chain terminator of DNA synthesis by retro virus reverstranscriptase, and AZT was approved in USA in March, 1987 as the first remedy for symptomatic AIDS patients with a history of Pneumocystis carinii pneumonia or with a CD4(T4)lymphocyte cell count of less than 200. But, therapeutic dose of AZT leads to many severe significant side effects such as anemia, leukopenia, neutropenia and occasional thrombocytopenia, probably delivered from AZT-induced bone marrow suppression. If a new drug can prescribe with small dose of AZT and the combination therapy is effective for AIDS or ARC or LA patients without severe side effects, this drug will be very useful for patients with AIDS or ARC or LA.

To overcome the above disadvantage of AZT, the present inventors conducted an intensive research and found FK-565 exhibits a marked and significant effect against Friend leukemia virus by combining AZT. From this fact, dosage of AZT in AIDS, ARC and LA treatments can possibly be reduced by combining AZT and as a result of it, side effects of AZT as mentioned above can possibly be reduced by using AZT in combination with FK-565, without reducing the effect of AZT.

FK-565 and its pharmaceutically acceptable salt are the known ones possessing an enhancing activity of immune response (cf. U.S. Pat. No. 4,322,341) and an anti-viral activity (cf. U.S. Pat. No. 4,666,889).

The chemical structure of FK-565 is as follows:

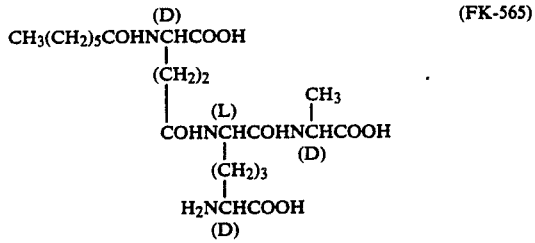

The pharmaceutically acceptable salt of the FK-565 is for example, an organic or inorganic salt such as sodium, salt, potassium salt, calcium salt, ammonium salt, ethanolamine salt, triethylamine salt, dichlorohexylamine salt, or an acid addition salt with an organic or inorganic acid, such as acetate, trifluoroacetate, lactate, maleate, fumarate, tartrate, citrate, methanesulfonate, hydrochloride, sulfate, nitrate or phosphate.

The composition for prevention and (or) treatment of AIDS or ARC or LA according to this invention can be used in various dosage forms which may, for example, be solid, semi-solid or liquid preparations containing the effective ingredient (i e. FK-565 or its pharmaceutically acceptable salt and AZT) of this invention in admixture with an organic or inorganic vehicle or excipient suitable for external, oral or parenteral administration The effective ingredient is used in combination with a non-toxic, pharmaceutically acceptable vehicle or carrier which is commonly employed in the production of tablets, pellets, capsules, suppositories, solutions, emulsions, suspensions and so forth. Among the useful vehicles and carriers are water, glucose, lactose, gum arabic, gelatin, mannitol, starch paste, magnesium trisilicate, talc, methylcellulose, polyethylene glycol, corn starch, keratin, colloidal silica, potato starch, urea, and other substances suitable for the production of solid, semi-solid or liquid pharmaceutical preparations. In addition to such a vehicle or carrier, there may also be employed an adjuvant, stabilizer, viscosity builder or thickener, colorant, flavor and so forth. The compositions for prevention and (or) treatment of AIDS or ARC or LA may also contain a preservative or/and an antibacterial agent so that the activity of the effective ingredients can be preserved. The effective ingredient compounds are contained in such a pharmaceutical composition in a sufficient amount for the production of desirable therapeutic effects against the progress or actual condition of a disease concerned.

For use in human beings, such a composition for prevention and (or) treatment of AIDS or ARC or LA is desirably administered intravenously, subcutaneously, intramuscularly or orally. The dosage or therapeutically effective dose of the effective ingredients of this invention, namely the FK-565 or a pharmaceutically acceptable salt thereof and AZT, depends on the age and condition of the patient to be treated.

The ratio of FK-565 or its pharmaceutically acceptable salt and AZT in the composition may vary with the symptoms of AIDS, ARC or LA patients, but may usually be 1:10-2000 by weight.

FK-565 or its pharmaceutically acceptable salt and AZT may administered to AIDS, ARC or LA patients as a composition comprising said two ingredient, and both ingredients may also be administered separately to such patients. Namely, AZT may first be administered, and then FK-565 or its pharmaceutically acceptable salt may be administered to patients, or alternatively FK-565 or its pharmaceutically acceptable salt may first be administered, and then AZT may be administered to patients in a certain period (generally in a week) after administration of FK-565 or its pharmaceutically acceptable salt.

In case that the effective ingredient, FK-565 or its pharmaceutically acceptable salt and AZT is separately administered to patients, such ingredients can each be used in the same dosage forms as previously illustrated for the composition.

In case that both two ingredients are separately administered to patients, the dosage or therapeutically effective dose of FK-565 or its pharmaceutically acceptable salt and AZT depends on the age and condition of the patient to be treated, but FK-565 or its pharmaceutically acceptable salt is generally used, for example, 1-4 times, preferably 2 times per week at a dose level of about 10-1000 μg per kilogram body weight of human being, and AZT is generally used, for example, 3-8 times, preferably 6 times per day at a dose level less than 3.3 mg per kilogram body weight of human being.

The following tests are given for illustrating this invention. In this illustration of effectiveness of FK-565 and AZT, the present inventors used Friend leukemia virus (FLV, retro virus) in the following Tests of in vivo evaluation of a combination of FK-565 and AZT, the reasons for which are as follows:

1) FLV is a mouse retro virus which is akin to human immuno deficiency virus (HIV), the cause of AIDS.
2) AZT was shown to suppress significantly in mice infected with a same retro virus, Rauscher murine leukemia virus complex(RLV), and also to prolong significantly the survival time in such infected mice.
3) HIV infects only humans and chimpanzees.
4) AZT is effective in treatment of both diseases of RLV and HIV.
5) If the combination therapy is effective for FLV, a solid clue of this therapy for effective new therapy for the patient with AIDS or ARC can be presented.

Accordingly, effect of FK-565 and AZT against splenomegaly by FLV in mice is shown in the following Tests to evidence the effectiveness of FK-565 and AZT for AIDS treatment.

TEST 1

(1) Materials and Methods

Animals: Male C3H/HeN strain mice aged 5 weeks were used in groups of 10. The animals were housed in an isolation room at 21°-25° C. and supplied with food and water at libitum.

Virus and Induction of splenomegaly: Friend leukemia virus (FLV) was prepared as a 10% suspension of infected C3H/HeN spleen in Hank's balanced saline and was originally supplied by Kitazato University. Following centrifugation (7,000 rpm for 20 mins.) the virus preparation was frozen and stored at −70° C. 0.2 ml/head of FLV diluted 2-, 5-, or 10-fold to induce infection of varying severity was challenged intraperitoneally in mice.

Dosing schedules: FK-565 was given intravenously or orally in doses of 0.01 mg/kg to 1 mg/kg 4 hours after challenge and once on days 3, 7, 11 (total 4 doses). AZT was given 20 mg/kg and 5 mg/kg intraperitoneally 3 times a day on days 1 to 4, 7 to 11 (total 27 doses) after challenge.

Evaluation : The inhibitory percent of FK-565 or AZT on the development of splenomegaly was calculated as follows:

$$\% \text{ inhibition} = \left\{ 1 - \frac{\left(\begin{array}{c}\text{Spleen weight of}\\ \text{infected animals}\\ \text{treated with drug}\end{array}\right) - \left(\begin{array}{c}\text{Spleen weight of}\\ \text{healthy animals}\\ \text{treated with drug}\end{array}\right)}{\left(\begin{array}{c}\text{Spleen weight of}\\ \text{infected control}\end{array}\right) - \left(\begin{array}{c}\text{Splene weight of}\\ \text{healthy control}\end{array}\right)} \right\} \times 100$$

(2) Results

Test results are shown in the following Tables 1 and 2.

TABLE 1

Effect of FK-565 and AZT in combination against splenomegaly by Friend leukemia virus in mice --- Severe infection, FK565; i.v. route ---

| Dose (mg/kg) AZT | Dose (mg/kg) FK-565 | Spleen weight (mg) | Inhibition % |
|---|---|---|---|
| Alone | | | |
| 20 | — | 944.0 ± 104.9* | 38.1 |
| 5 | — | 1107.8 ± 158.3 | 24.8 |
| — | 1 | 947.0 ± 124.1# | 46.5 |
| — | 0.1 | 1038.0 ± 176.8* | 37.0 |
| — | 0.01 | 1047.0 ± 106.1# | 36.4 |
| Combination | | | |
| 20 | 1 | 493.0 ± 70.7## | 73.1 |
| 20 | 0.1 | 574.0 ± 103.8## | 71.8 |
| 20 | 0.01 | 650.0 ± 111.3## | 62.8 |
| 5 | 1 | 832.0 ± 79.6## | 45.6 |
| 5 | 0.1 | 1027.0 ± 114.7# | 36.5 |
| 5 | 0.01 | 808.0 ± 104.3## | 49.8 |
| Control | | 1455.0 ± 44.8 | — |

Mouse: C3H/HeN, 5W, Male, n = 10
Infection: Friend leukemia virus, 0.2 ml/head of 2-fold dilution, i.p.
Schedule of dosing: FK-565, i.v. +4h, 3d, 7d, and 11d. (once a day, total 4) AZT, i.p. 3/day from 24 hours after infection, +1–4d. and 7–11d. (total 27)
Observation: 14 days after infection
Significant difference from control (*p < 0.05, #p < 0.01, ##p < 0.001)

TABLE 2

Effect of FK-565 and AZT in combination against splenomegaly by Friend leukemia virus in mice --- Severe infection, FK565; p.o. route ---

| Dose (mg/kg) AZT | Dose (mg/kg) FK-565 | Spleen weight (mg) | Inhibition % |
|---|---|---|---|
| Alone | | | |
| 20 | — | 944.0 ± 104.9* | 38.1 |
| 5 | — | 1107.8 ± 158.3 | 24.8 |
| — | 1 | 984.0 ± 144.8# | 38.9 |
| — | 0.1 | 1133.0 ± 170.0** | 27.8 |
| Combination | | | |
| 20 | 1 | 1052.0 ± 556.9 | 30.7 |
| 20 | 0.1 | 705.0 ± 122.2## | 60.5 |
| 5 | 1 | 857.0 ± 126.3# | 45.7 |
| 5 | 0.1 | 950.0 ± 105.9## | 38.0 |
| Control | | 1455.0 ± 44.8 | — |

Mouse: C3H/Hen, 5W, Male, n = 10
Infection: Friend leukemia virus, 0.2 ml/head of 2-fold dilution, i.p.
Schedule of dosing: FK-565, p.o. +4h, 3d, 7d, and 11d. (once a day, total 4) AZT, i.p. 3/day from 24 hours after infection, +1–4d. and 7–11d. (total 27)
Observation: 14 days after infection
Significant difference from control (**p < 0.1, *p < 0.05, #p < 0.01, ##p < 0.001)

TEST 2

A test was conducted according to the same method as that of Test 1 excepting doses of FK-565 and AZT which are shown as follows:

FK-565 (mg/kg): 1, 0.01
AZT (mg/kg): 160, 40, 10, 2.5, 0.63
Results are shown in the Table 3.

TABLE 3

Effect of FK565 and AZT in combination against splenomegaly by FLV in mice

| AZT Dose (mg/kg) | AZT alone Spleen (mg) | (%) | With FK-565 1 mg/kg Spleen (mg) | (%) | With FK-565 0.01 mg/kg Spleen (mg) | (%) |
|---|---|---|---|---|---|---|
| 160 | 162 ± 11.5## | 97.4 | 220 ± 8.3## | 92.0 | 240 ± 10.3## | 90.7 |
| 40 | 267 ± 51.6## | 81.1 | 231 ± 5.3## | 89.2 | 257 ± 20.1## | 86.1 |
| 10 | 519 ± 130.6* | 49.3 | 272 ± 9.4## | 83.6 | 256 ± 20.3## | 84.1 |
| 2.5 | 605 ± 134.9* | 38.3 | 352 ± 62.5## | 73.4 | 439 ± 82.9## | 60.2 |
| 0.63 | 633 ± 67.6# | 33.3 | 339 ± 60.3## | 72.2 | 521 ± 60.5## | 49.3 |
| 0 | N.D. | | 487 ± 47.3## | 55.3 | 750 ± 119.0* | 19.6 |
| Infected control | | | 894 ± 34.2 | | | |
| Normal control | | | 128 ± 8.8 | | | |

Mouse: C3H/HeN, 5W, n = 10
Infection: Friend leukemia virus, 0.2 ml/head of 2-fold dilution, i.p.
Dosing schedule: FK-565, i.v. +4h, 3, 7, and 11d. (total 4) AZT, i.p. +1–4d, and 7–11d. (3/day) (total 27)
Observation: 14 days after infection
Significant difference from control (*p < 0.05, #p < 0.01, ##p < 0.001)

As seen from Tables 1 to 3, an inhibitory activity of AZT against FLV splenomegaly is increased by combining FK-565.

TEST 3

(1) Materials and Methods

Friend leukemia virus (FLV) was prepared as a 20% suspension of infected C3H/HeN spleen in Hank's balanced saline and 0.2 ml/head of the FLV preparation was challenged intraperitoneally to mice in groups of 12. The viruses were challenged in amounts large enough to cause death within a short time.

FK-565 (1, 0.01 mg/kg) was given intravenously once a day on days 1, 4, 7, 11, 14, 18, 21 and 25 (total: 8 doses). AZT (100, 20, 4 mg/kg) was given intraperitoneally twice a day on days 1 to 4, 7 to 11, 14 to 18 and 21 to 25 (total: 38 doses).

The mice were given the two drugs according to the same dosing schedules. The tested mice were observed for mortalities for 42 days after challenge and the survival rates were determined.

(2) Results

The test results are shown in the following Table 4.

TABLE 4

The survival rate of mice treated by FK-565 and AZT alone or in combination in FLV infection.

| Dose (mg/kg/time) | AZT 100 | AZT 20 | AZT 4 | AZT 0 |
|---|---|---|---|---|
| FK-565  1 | 67* | 42* | 42* | 17 |
| 0.01 | 58* | 33* | 25* | 8 |
| 0 | 50* | 25* | 0 | |

Statistical significant differences from control were calculated by Chi-square test (*p < 0.05).

As seen from Table 4, the survival rate of mice treated by AZT in FLV infection is synergisticly increased by combining FK-565.

Accordingly, dosage of AZT in AIDS, ARC and LA treatments can possibly be reduced by combining FK-565 or its pharmaceutically acceptable salt and as a result of it, side-effects of AZT can possibly be reduced, and therefore this combination therapy is expected to be useful for patients with AIDS, ARC or LA.

Further, the survival of patients with AIDS, ARC and (or) LA is expected to be prolonged by using FK-565 or its pharmaceutically acceptable salt and AZT.

We claim:

1. A method for treatment of Lymphadenopathy which comprises administering FK-565 or its pharmaceutically acceptable salt and AZT in a ratio of about 1:10–2000 by weight to an individual in need thereof.

2. A method for treatment of Lymphadenopathy which comprises intravenously administering FK-565 or its pharmaceutically acceptable salt 1–4 times per week at a dose level of about 10–1000 μm per kilogram body weight and administering AZT orally 3–8 times per day at a dose level less than 3.3 mg per kilogram body weight to an individual in need thereof.

3. A method for prolongation of the survival of patients with Lymphadenopathy, which comprises administering to the patients FK-565 or its pharmaceutically acceptable salt and AZT in a ratio of about 1:10–2000 by weight.

4. A method for prolongation of the survival of patients with Lymphadenopathy, which comprises administering intravenously to the patients FK-565 or its pharamceutically acceptable salt 1–4 times per week at a dose level of about 10–1000 μm per kilogram body weight of the patients, and administering orally to the patients AZT 3–8 times per day at a dose level less than 3.3 mg per kilogram body weight of the patients.

5. A method for decreasing the effective amount of AZT during treatment of patients with Lymphadenopathy, which comprises administering to the patients FK-565 or its pharmaceutically acceptable salt and AZT in a ratio of about 1:10–2000 by weight.

6. A method for decreasing the effective amount of AZT during treatment of patients with Lymphadenopathy, which comprises intravenously to the patients FK-565 or its pharamceutically salt 1 to 4 times per week at a dose level of 10–1000 μm per kilogram body weight of the patients, and administering orally to the patients AZT 4 to 8 times per day at a dose level less than 3.3 mg per kilogram body weight of the patients.

7. A method for decreasing the effective amount of AZT during treatment of patients with Lymphadenopathy, which comprises reducing the AZT dose by using AZT in combination with FK-565 or its pharmaceutically acceptable salt.

* * * * *